(12) United States Patent
Taerum et al.

(10) Patent No.: US 9,443,303 B2
(45) Date of Patent: Sep. 13, 2016

(54) IMAGE DISPLAY OF A CENTERLINE OF TUBULAR STRUCTURE

(71) Applicant: Calgary Scientific Inc., Calgary (CA)

(72) Inventors: Torin Arni Taerum, Calgary (CA); Jonathan Neil Draper, Calgary (CA); Robert George Newton, Calgary (CA)

(73) Assignee: Calgary Scientific Inc., Calgary, AB (CA)

( * ) Notice: Subject to any disclaimer, the term of this patent is extended or adjusted under 35 U.S.C. 154(b) by 0 days.

(21) Appl. No.: 14/273,966

(22) Filed: May 9, 2014

(65) Prior Publication Data
US 2014/0363065 A1 Dec. 11, 2014

Related U.S. Application Data

(63) Continuation-in-part of application No. 13/466,308, filed on May 8, 2012.

(60) Provisional application No. 61/532,700, filed on Sep. 9, 2011, provisional application No. 61/561,582, filed on Nov. 18, 2011.

(51) Int. Cl.
*G06T 7/00* (2006.01)
*A61B 5/02* (2006.01)
(Continued)

(52) U.S. Cl.
CPC ......... *G06T 7/0012* (2013.01); *A61B 5/02014* (2013.01); *G06T 7/0083* (2013.01); *G06T 19/00* (2013.01); *A61B 6/466* (2013.01); *A61B 6/481* (2013.01); *A61B 6/5205* (2013.01); *A61B 8/466* (2013.01); *A61B 8/481* (2013.01); *A61B 8/483* (2013.01); *A61B 8/5207* (2013.01); *G06T 2207/10081* (2013.01);

(Continued)

(58) Field of Classification Search
CPC .......... A61B 5/00; A61B 8/00; A61B 8/466; A61B 8/481; A61B 8/483; A61B 8/5207; A61B 6/00; A61B 6/5205; A61B 6/466; A61B 6/481
See application file for complete search history.

(56) References Cited

U.S. PATENT DOCUMENTS

| | | |
|---|---|---|
| 6,782,284 B1 | 8/2004 | Subramanyan et al. |
| 7,369,691 B2 | 5/2008 | Kondo et al. |

(Continued)

FOREIGN PATENT DOCUMENTS

| | | |
|---|---|---|
| WO | 2005/055496 | 6/2005 |
| WO | 2010/068481 | 6/2010 |

OTHER PUBLICATIONS

Aylward, Stephen R., "Initialization, Noise, Singularities, and Scale in Height Ridge Traversal for Tubular Object Centerline Extraction," IEEE Transactions on Medical Imaging, vol. 21, No. 2, Feb. 2002, pp. 61-75.

*Primary Examiner* — Peter Luong
(74) *Attorney, Agent, or Firm* — Meunier Carlin & Curfman LLC

(57) ABSTRACT

Systems and methods for determining a centerline of a tubular structure from volumetric data of vessels where a contrast agent was injected into the blood stream to enhance the imagery for centerlining. Given a 3D array of scalar values and a first and second point, the system and methods iteratively find a path from the start position to the end position that lies in the center of a tubular structure. A user interface may be provided to visually present and manipulate a centerline of the tubular structure and the tubular structure itself.

20 Claims, 19 Drawing Sheets

(51) Int. Cl.
*G06T 19/00* (2011.01)
*A61B 6/00* (2006.01)
*A61B 8/00* (2006.01)
*A61B 8/08* (2006.01)

(52) U.S. Cl.
CPC ............... *G06T 2207/10088* (2013.01); *G06T 2207/10136* (2013.01); *G06T 2207/20076* (2013.01); *G06T 2207/30101* (2013.01); *G06T 2210/41* (2013.01); *G06T 2219/028* (2013.01)

(56) References Cited

U.S. PATENT DOCUMENTS

| | | | |
|---|---|---|---|
| 8,162,835 B2* | 4/2012 | Ichikawa et al. | 600/443 |
| 2003/0053697 A1 | 3/2003 | Aylward et al. | |
| 2007/0274579 A1 | 11/2007 | Cai et al. | |
| 2008/0249755 A1 | 10/2008 | Tek et al. | |
| 2010/0131887 A1 | 5/2010 | Salazar-Ferrer | |
| 2011/0150274 A1* | 6/2011 | Patwardhan et al. | 382/103 |

* cited by examiner

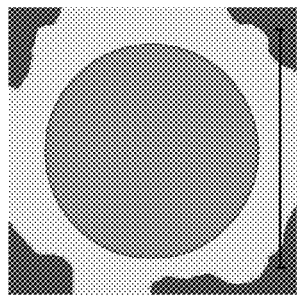
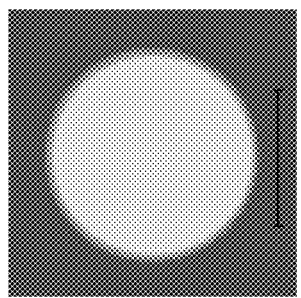
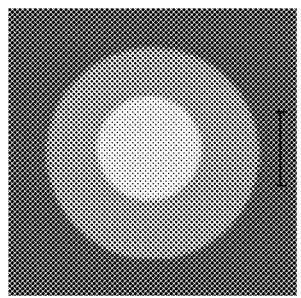
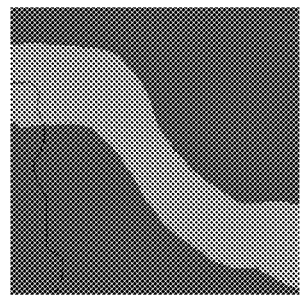
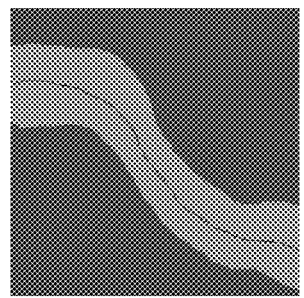
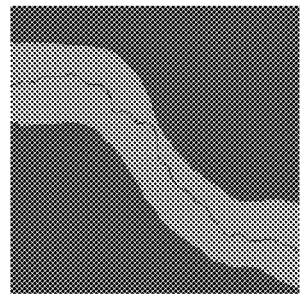
FIG. 4A  FIG. 4B  FIG. 4C  FIG. 4D
FIG. 5A  FIG. 5B  FIG. 5C  FIG. 5D

IMAGE DISPLAY OF A CENTERLINE OF TUBULAR STRUCTURE

CROSS-REFERENCE TO RELATED APPLICATIONS

This application claims priority to U.S. patent application Ser. No. 13/466,308, filed May 8, 2012, entitled "IMAGE DISPLAY OF A CENTERLINE OF TUBULAR STRUCTURE," which claims priority to U.S. Provisional Patent Application No. 61/532,700, filed Sep. 9, 2011 and U.S. Provisional Patent Application No. 61/561,582, filed Nov. 18, 2011, each entitled "Image Display of a Centerline of Tubular Structure." Each application above is incorporated herein by reference.

BACKGROUND

With the advent of sophisticated medical imaging modalities, such as magnetic resonance, computed tomography, ultrasound, and cone-beam X-ray imaging, three-dimensional (3D) volumetric data sets can be reconstructed from a series of two-dimensional (2D) slices of an anatomical structure taken around an axis of rotation. Such 3D volumetric data may be displayed using volume rendering techniques so as to allow a physician to view any point inside the anatomical structure, without the need to insert an instrument inside the patient's body.

To detect, diagnose, and treat blood vessel pathologies, physicians and other healthcare professionals rely on the visual examination of 3D images and multiple 2D projection or cross sectional images. Recent advances in the medical image processing field have made available some software tools for semi-automated quantification of vascular diseases. Software tools for semi-automated quantification of the severity of blood vessel stenosis, and the size of aneurysms are available for use today on some clinical image processing workstations. These tools typically analyze blood vessels through an idealized model of a blood vessel, such as a tubular model with possible branching. One of general steps for analyzing the shape of blood vessels is the extraction of the centerline of these vessels. For diseases like aneurysms or stenosis, the profile of the blood vessel diameter along the centerline abnormally expands or shrinks, respectively.

SUMMARY

Disclosed herein are systems and methods for determining a centerline of a tubular structure. The systems may include a computing device and the methods may be performed by a processor executing within the computing device. Volumetric data of vessels may be provided where a contrast agent was injected into the blood stream to enhance the imagery for centerlining. Given a 3D array of scalar values and a first and a second point (seed points), the system and methods iteratively find a path from the first point to the second point that lies in the center of a tubular structure by transforming the data associated with the curves. A user interface may be provided to visually present and manipulate a centerline of the tubular structure and the tubular structure itself.

In accordance with some implementations, the methods may include receiving, at a computing device, volumetric data representative of the tubular structure and a selection of a first point and a second point along a length of the tubular structure; initializing a minimal range of data values associated with a cross section of the tubular structure; and iteratively generating positions associated with two discrete curves from each point toward the other point, the positions initially moving along a direction vector defined at each point. Iteratively generating positions may include defining a cross section in a plane of the tubular structure; and choosing a next point on each of the two discrete curves in accordance with a smallest area among plural cross sections determined at each next point on each of the two discrete curves. For each of the two discrete curves, the method may include moving in a direction normal to the cross section having the smallest area; determining if the discrete curves have terminated; if the discrete curves have terminated, then determining if a length of a result of a curve in a present iteration is shorter than a length of a curve as determined in a previous iteration; and caching the result of the curve in the present iteration pass if it is determined that the length of the result of the curve in the present iteration is shorter, otherwise maintaining the length of the curve as determined in the previous iteration. Next, the method may include increasing the range of data values for a next iteration; and terminating the iterative process when a length of a joined curve is longer than a joined curve of the previous iteration, the joined curve of the previous iteration corresponding to the centerline, otherwise returning to iteratively generating positions.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 4A-4D illustrate a cross section of the tubular structure and varying data ranges of cross sectional areas from small to large;

FIGS. 5A-5D illustrate a resulting centerline derived from the associated data range;

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for determining a centerline of a tubular vessel, detecting branches and contouring of a tubular vessel, and for determining a location of an aneurysm, it will become evident to those skilled in the art that the implementations are not limited thereto.

Figure 1:
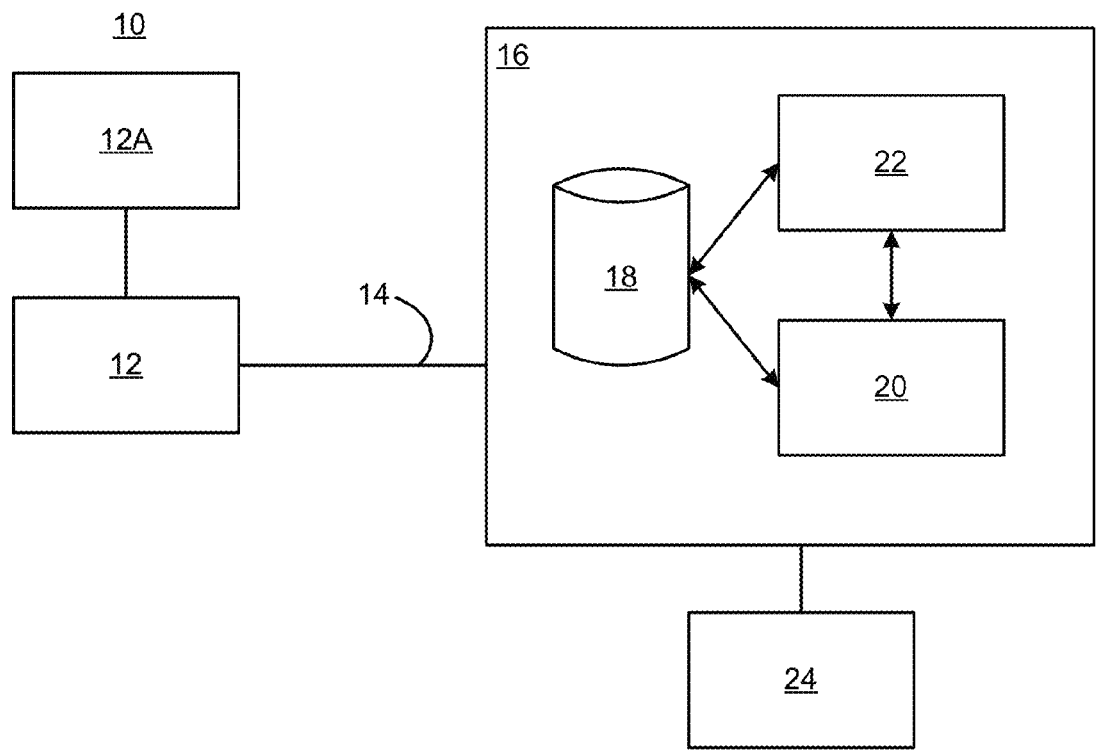
FIG. 1 is a simplified block diagram of a medical imaging system.

FIG. 1 is a simplified block diagram of a medical imaging system 10. The system 10 comprises a medical imaging scanner 12 that acquires image data of a patient under examination. The scanner 12 may use any appropriate imaging modality to acquire the image data, for example, magnetic resonance, computed tomography, ultrasound, and X-ray imaging. The scanner 12 may acquire raw image data from multiple scanned views of the region of interest of the patient, reconstruct the images, and produce image data signals for the multiple views. The image data signals may be in Digital Imaging and Communications in Medicine (DICOM) format. Other formats may also be used.

The imaging scanner 12 is operably connected to a computer system 12a that controls the operation of the scanner 12 and, via a communication channel 14, to an image processing system 16 that processes the image data signals utilizing appropriate image processing software applications. The communication channel 14 may be a direct peer-to-peer connection; a network connection such as LAN, a WAN, or the Internet; a wired or wireless connection, etc. The image processing system 16 has an image data archive or database 18, an application server 20, and a user workstation 22. The components of the image processing system 16 are interconnected via a communications network that may be implemented by physical connections, wireless communications, or a combination. The image data archive or database 18 is adapted to store the image data signals that are produced by the image scanner 12 as well as the results of any additional operations on the image data signals by the other components of the image processing system 16. The image data archive or database 18 may be a Picture Archiving and Communications System (PACS). Other types of image data archives or databases may also be used.

The user workstation 22 is adapted to control the operation of the imaging processing system 16 and its various components. The user workstation 22 may interact with the application server 20 and the various image processing software applications that are stored in, or are accessible by, the application server 20. The user workstation 22 may be any computing device, such as a desktop computer, dedicated workstation, laptop, notebook, table computing device, mobile device (e.g., wireless handheld smartphone), etc. The user workstation 22 communicates via either a wired or wireless connection.

The application server 20 also manages and coordinates the image data sets among the image processing applications. The image processing applications may include, for example, visualization applications, computer-aided diagnosis (CAD) applications, medical image rendering applications, anatomical segmentation applications, or any other type of medical image processing application. The image processing applications may also include the methods of the present invention. The image data archive or database 18, applications server 20, and the user workstation may also each be connected to a remote computer network or computing device 24 (e.g., a remote device having the characteristics of the workstation 22, as noted above) for communication purposes or to access additional data or functionality. The workstation 22 may comprise appropriate user interfaces, like displays, storage media, input/output devices, etc.

The various components of the imaging system 10 are conventional and well known components, and may be configured and interconnected in various ways as necessary or as desired. The imaging system 10 and, in particular, the image processing system 16 is adapted to permit the imaging system 10 to operate and to implement methods in accordance with the present disclosure, for example, as shown in FIG. 3.

Figure 2:
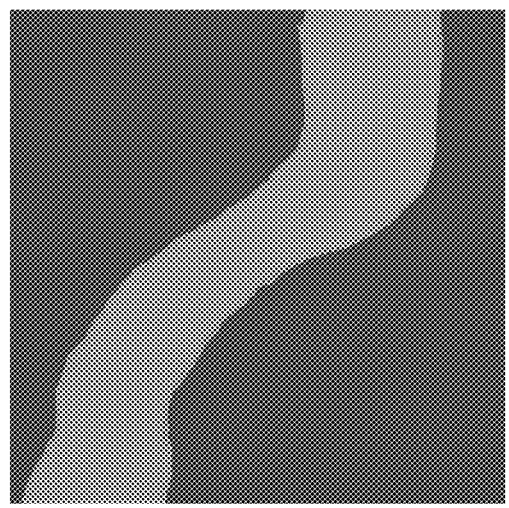
FIG. 2 is an image of a tubular structure.

FIG. 2 illustrates an image of a tubular structure. As shown in FIG. 2, the tubular structure may be a 2D view of a vessel within the body. The structure may be processed by the image processing system 16 such that it has different pixel intensities, as compared to the surrounding tissue. The image may be presented to a user on a high resolution display of, e.g., the workstation 20, or provided remotely to a device via an application server connected to the image processing system 16 that communicates imagery via a network connection to the remote device.

Figure 3A:
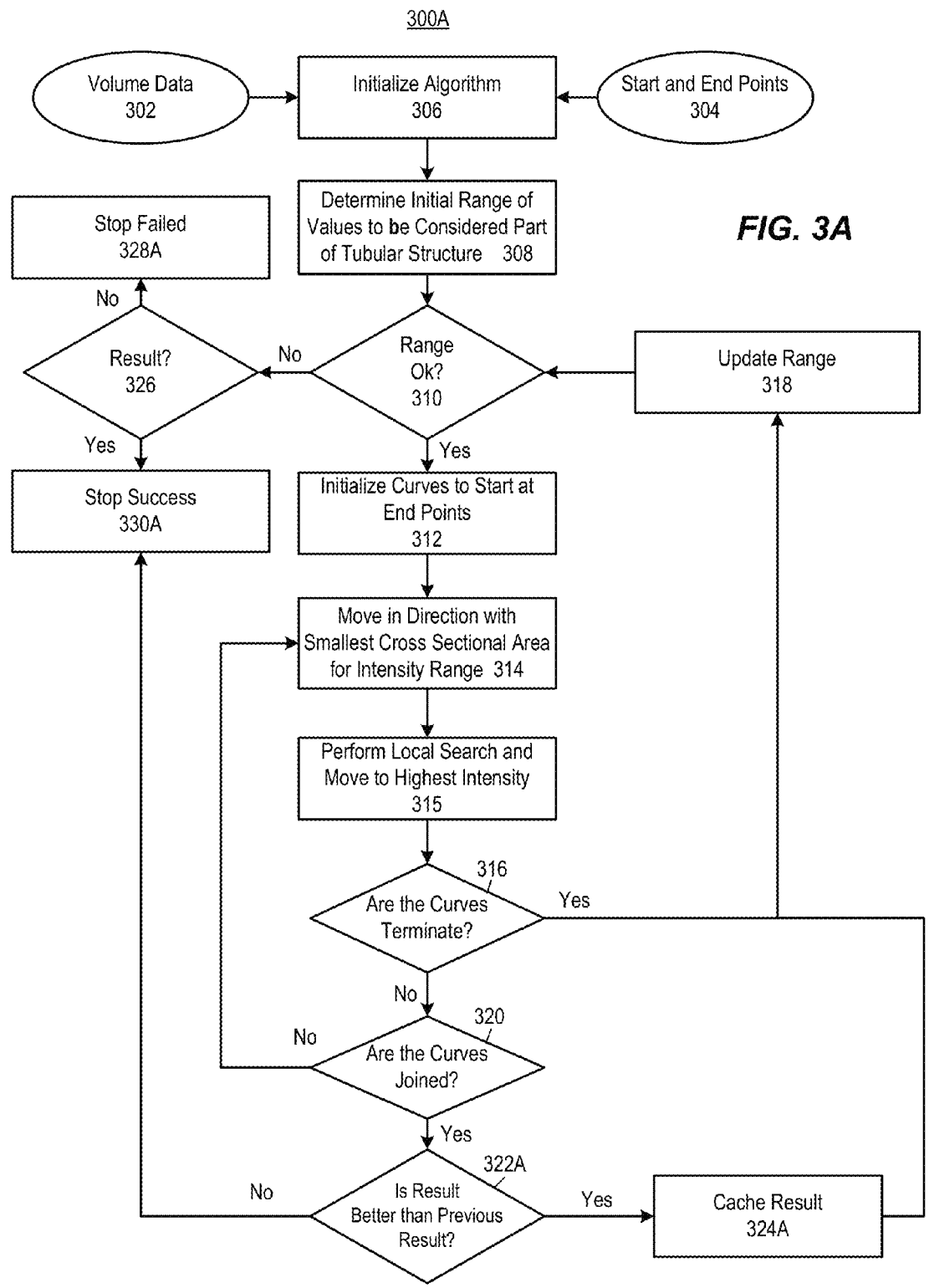
FIGS. 3A-3B illustrate example operational flow diagrams of processes performed to determine a centerline of a tubular structure, such as that shown in FIG. 2.
Figure 3B:
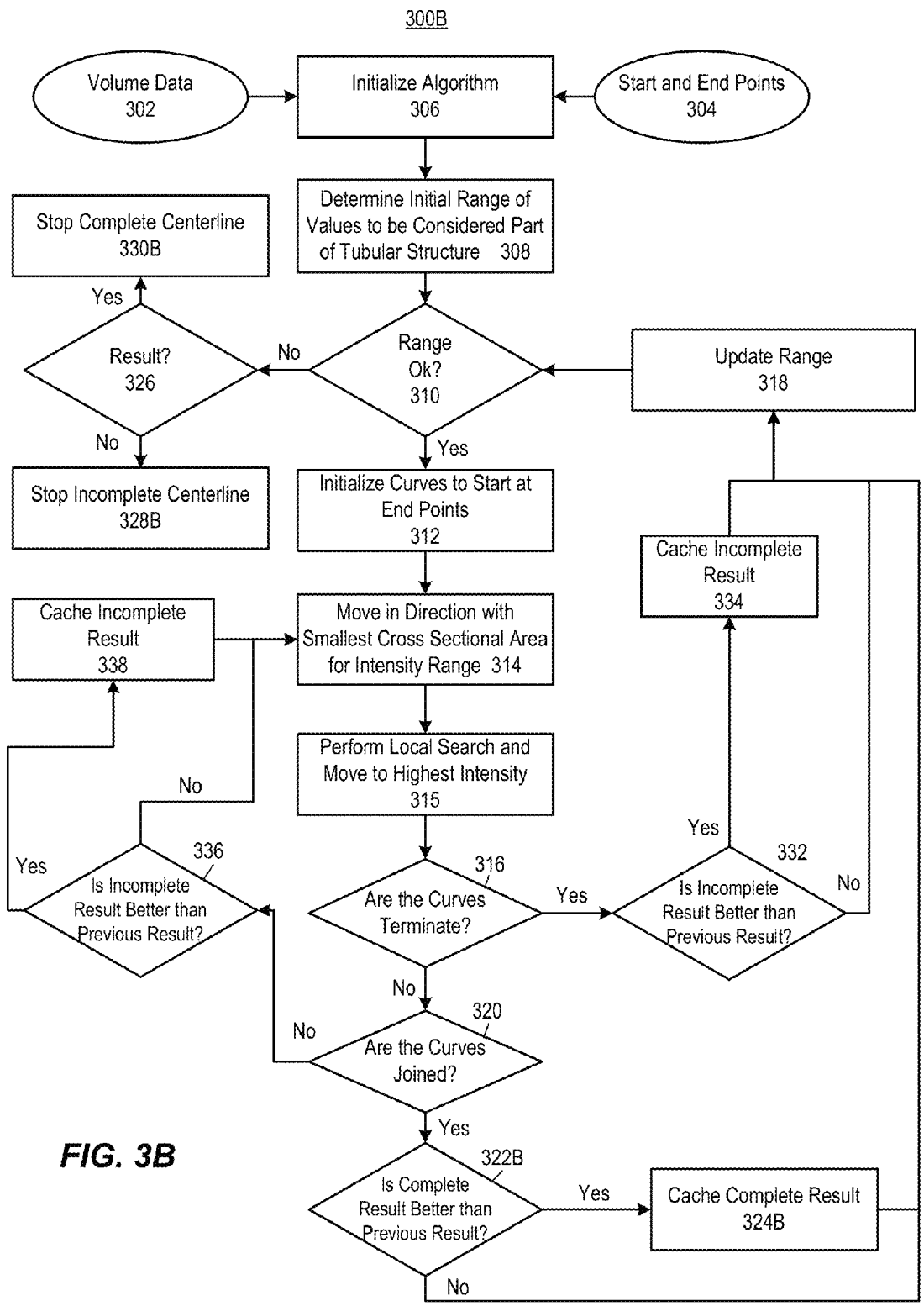

FIGS. 3A-3B illustrate example operational flow diagrams of processes performed to determine a centerline of a tubular structure, such as that shown in FIG. 2. In general, the processes of FIGS. 3A-3B identify the centerline and cross sectional contours of tubular structures that may be found in volumetric data, such as that shown in FIG. 2. The volumetric data may be derived from magnetic resonance or computed tomography imagery of vessels where a contrast agent was injected into the blood stream to enhance the imagery for centerlining. Given a 3D array of scalar values and a first and a second point (seed points), the processes will find a path from the first point to the second point that lies in the center of a tubular structure. The first point and the second point may be any points along the tubular structure. The border of the tubular structure is defined by a large gradient magnitude in the scalar intensities. However, the definition of the tubular structure is not always perfect in that the intensity values that make up the inside of the tubular structure may not be known which can make finding the centerline difficult.

With reference to FIG. 3A, a first example operational flow 300A begins when a 3D array of scalar values (i.e., the volume data) (S302) is provided and two input points, or seed points, within the volume (vessel) are selected as a first point and a second point (S304). The scalar values provided at S302 are pixel intensity values. A user may be presented with a 2D display of the 3D array, where the 2D display is slice along the axial, sagittal or coronal planes (three orthogonal views). From the 2D display, the user may indicate the two input points at S304 when viewing the imagery using, e.g., a mouse. In some implementations, the two input points may be provided automatically by another system.

At S306, the algorithm is initialized by evaluating statistics local to the two input points. In particular, at S308, at the first point and the second point, the area of the tubular structure at that point and the associated range of data values are determined by detecting the steep gradient at the wall of the tubular structure. For example, the cross-section area may be measured for increasing values of data range. The correct cross-sectional area and associated range is selected by locating the range of values that provides an appropriate minimum in the expansion of the area with changes in the range. Other metrics, such as a standard deviation of the data values may be used to examine the data values. From these statistics, an initial range of values (pixel intensities) is calculated that will be considered part of the tubular structure.

The range may be constrained so that it will initially be very small with respect to the full range of the data in order to reduce errors where a vessel is near another structure of potentially overlapping pixel intensities, such as bones, the base of the skull, etc. As described below, this enables the methods of the present disclosure to track a centerline that is parallel or adjacent to a bony structure (e.g., the carotid siphon). In addition, a smaller range of values will help ensure that if the process does not succeed, it fails quickly. Throughout the process described below, the range may be expanded or limited, as necessary.

At S310, the flow enters an iterative loop that executes so long as the range has changed less than a configurable number of times (see, below). The process attempts to generate two discrete curves, represented as Non-Uniform Rational B-Spline (NURBS) curves that start at the two input points and join at some position within the volume. The two curves are used to increase the likelihood of finding a curve that connects the two points when there are bifurcations, trifurcations, or more complex branches. For example, if one of the curves goes down a wrong branch, then the curve starting at the other point will join at the point where the first curve branches. In yet other circumstances, the curves may not join indicating that both curves may have traveled down different branches of the tubular structure.

At S312, for each range, the curves are initialized to start at the input points, i.e., one from the first point and one from the second point. At S314, the initial direction vector for each curve is towards the other input point. Using the initial point and direction, a plane is defined in the volume perpendicular to the direction and passing through the point (a current point). This plane describes a cross section of the tubular structure. In order to choose the next point to add to the curve, the direction is perturbed slightly in several directions. For example, the direction may be perturbed in, e.g., sixteen directions. Each of the perturbed directions results in another cross section. For each of these cross sections the area of the tubular structure is measured. The area is measured based on the requirement that values be connected and within the current range. The direction normal to the cross section with the smallest area is chosen as the direction to move.

At S315, a local search may be performed to determine and move to a pixel having a highest intensity. For example, in the case of magnetic resonance (MR) data where the vessel is narrow, it is likely that the pixel with the highest intensity value in the local region is the center of the vessel. To account for instances where a path defined by the above process is not passing through that pixel, the local search looks for a pixel having a more intense value. The locality of the search may be limited to 2 minimum spacing units from the current point. If a pixel (or pixels) is found having a higher intensity, the path is moved to the pixel having the highest intensity.

At S316, it is determined if the curves have terminated. This may be tested by determining if the intensity value at this new position is not within the current range. If so, the curve is terminated. For example, if the intensity at the new position was greater, it is possible that the new position is in bone. If at S316 the curves have not terminated, then the intensity value at this position is within the current range. As such, the point is added to the curve. The curves are then tested at S320 to see if they have joined. If the curves are not joined, the process of measuring the smallest cross sectional area to determine the next direction at S314 is repeated using the new position and direction. In accordance with some implementations, the curves may be terminated if a resulting total length of the two distinct curves reaches a predetermined length, e.g., 3000 mm.

If the curves are joined at S320, it is possible that the resulting curve may not follow the center of the tubular structure; rather it may follow a tortuous path inside the tubular structure. To alleviate this condition, the result may be cached at S324A (passing through S322A in a first loop), and the range increased at S318 to run the process again (S310-S320). The amount that the range is increased depends on the initial range, the full range of the values in the dataset, how much the range was increased the last time the range was increased, etc. Thus, the value of range that is used for the next attempt through the loop is updated in accordance with the details of the termination of the current attempt along with a history the previous attempts. As will be shown in FIGS. 4A-4D and 5A-5D, changing the range enables the process of FIG. 3 to take advantage of the principal that a curve following the center of a tubular structure is guaranteed to be shorter than one that follows a tortuous path inside the tubular structure. Thus, after running through the process S310-S320 a subsequent time, if the result of the process is "better" at S322A, then the result may cached at S324A, and so on. A "better" result is when the length of the curve is shorter than the length of the curve as determined in the previous pass through the loop. The process continues until it fails to find a curve connecting the two points, or the resulting curve is longer than a previous result, which likely means the range has become too large (S330A).

Returning back to S316, if both curves are terminated, the process flows to S318, where the range is increased and the curves are reinitialized to start over at S310. When the loop returns to S310, it is determined if the range is no longer okay. The test at S310 determines if the range has grown to greater than five times the initial range or if more than 20 iterations of the loop have been performed. If the range is no longer okay, then it is determined if there is a result at S326. The result may be determined to be a success at S330A or a failure at S328A. If the range is okay at S310, then the flow continues at S312, as described above.

As illustrated in FIG. 3A, the operational flow 300A may result in two outcomes, (1) a centerline is obtained at S330A, or (2) no centerline is obtained because the two ends do not join after multiple attempts (S328A). The operational flow 300A may be implemented within systems that are examining vessels with issues that can interfere with the centerlining process. For example, the vessels may have stenosis. As such, a second example operational flow 300B (FIG. 3B) produces either a complete centerline or a partial centerline.

As will be described, the operational flow 300B includes operations that iteratively look for the best incomplete result (i.e., the process compares each incomplete result with the previous incomplete result) and maintains the best incomplete result in a cache. Rather than returning no centerline (i.e., S328A), operational flow 300B returns a partial centerline from the cached incomplete results. If necessary, or as desired, a user may further manually edit the partial centerline.

With reference to FIG. 3B, the operational flow 300B will now be described. Operations that are the same as those introduced above with regard to FIG. 3A are referenced by the same reference numbers and are not repeated below for purposes of conciseness. The operational flow 300B begins with S302 and S304, and flows through S316, as described above.

At S316, it is determined if the curves have terminated. This may be tested by determining if the intensity value at this new position is not within the current range. If so, the curve is terminated. For example, if the intensity at the new position was greater, it is possible that the new position is in bone. If at S316 the curves have not terminated, then the intensity value at this position is within the current range. As such, the point is added to the curve. The curves are then tested at S320 to see if they have joined. If the curves are not joined, then, at S336, it is determined if the incomplete result is "better" than a previous result. Here, a "better" result is determined by looking for the centerline sections that result in the smallest gap between the two pieces of the curves. The determination at S336 may be made to keep track of the best incomplete result from the current iteration through the loop that begins at S310. If not, then the flow returns to S314. If the incomplete result is "better" than a previous result, then the "better" result is cached at 338, and the flow returns to S314. If the curves are joined at S320, then it is tested at S322B if the complete result is "better" than a previous result. If yes, then the result is cached at S324B, and the range increased at S318 to run the process again (S310-S320). If at S322B the complete result is not "better" than a previous, then the flow proceeds directly to S318.

Returning back to S316, if both curves are terminated, the process flows to S332, where it is determined if the incomplete result is "better" than a previous result. The determination at S336 may be made to compare the best incomplete result from the current iteration through the loop that begins at S310 with incomplete results of previous iterations. This determination may be made by applying the following relationship:

if (gap>=distance)

quality=0 otherwise quality=(distance−gap)×(distance−gap)/(distance× length), where:
distance=distance between the two starting points.
length=total length of the two sections (one from each endpoint).
gap=remaining distance between the final end points of the two centerline sections (i.e. the points that the two sections got to).
In the above, the quality ranges from 0 to 1, with 1 being the best theoretical quality achievable.
The above relationship favors partial centerlines that result in the smallest gap and which cover the distance achieved most efficiently (e.g., this is similar to the shortest length criteria for a complete centerline).

If at S336 the result is not "better," then the flow returns to S318 where the range is increased and the curves are reinitialized to start over at S310. If the incomplete result is "better" than a previous result, then the "better" result is cached at 334, and the flow returns to S318.

When the loop returns to S310, it is determined if the range is no longer okay. As noted above, the test at S310 determines if the range has grown to greater than five times the initial range or if more than 20 iterations of the loop have been performed. If the range is okay at S310, then the flow continues at S312, as described above. If the range is no longer okay, then it is determined if there is a result at S326. If yes, the result is determined to be a success at S330B or, if no, an incomplete result is provided S328B from the cached results.

Thus, to summarize the operational flows of FIGS. 3A-3B, an optimal result may be found when the curve connecting the two points is along the shortest path length constrained by the smallest range used to determine cross sectional areas. It is noted that sampling associated with the processes herein may be performed using trilinear interpolation.

FIGS. 4A-4D and 5A-5D show the effect of the changing ranges for cross sections and the resulting centerlines, respectively, to demonstrate the iterative flow of FIG. 3. As shown in FIGS. 4A and 5A, selecting a small range will often fail to find a complete centerline, as it typically results in a highly tortuous curve travelling inside the tubular structure. As the range increases (FIGS. 4B and 4C), the centerline becomes smoother (FIGS. 5B and 5C) and passes through the true center of the tubular structure (FIG. 5C). Once the range is too large (FIG. 4D) either a centerline will not be found or the length of the result will start to increase (see, FIG. 5D).

Once the centerline of a vessel is determined, contouring may be performed by taking cross-sections of the vessel at regular intervals. With the cross-sections, the edge of the tubular structure may be determined. Finding high quality contours that outline a tubular structure from a collection of cross sections may be problematic, as tubular structures may not exhibit a large gradient magnitude at their borders. In addition, tubular structures may contain bifurcations, trifurcations, or more complex branch structures that make finding high quality contours difficult. In using the results from contouring, it is possible that the contour produced at a branching of the vessel may be identified as a false positive for an aneurysm or stenosis, or may otherwise obscure important details.

Figure 6:
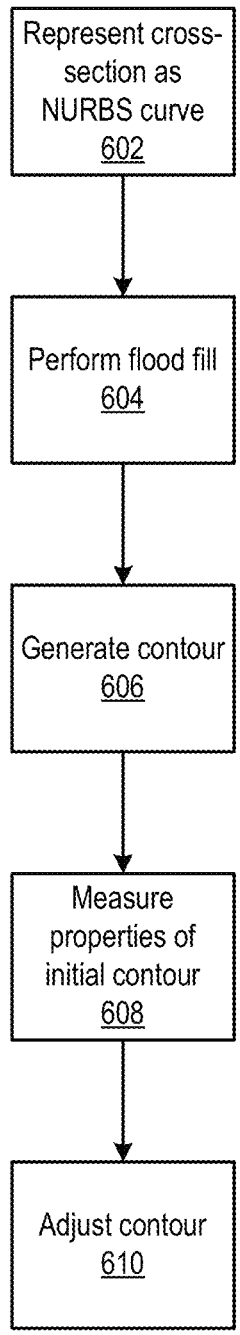
FIG. 6 illustrates an operational flow diagram of processes performed to generate a contour of the tubular structure and detect branches of the tubular structure, such as that shown in FIG. 2.

In accordance with aspects of the present disclosure, once a centerline is determined, various methods may be used to generate a contour. FIG. 6 illustrates an example operational flow diagram to generate a contour of the tubular structure and detect branches of the tubular structure. At S602, the cross section contour is represented as a NURBS curve. At S604, the initial contour for each cross section is found by performing a flood fill initiated at the center and constrained by the best range that was used in the centerline algorithm of FIG. 3. The resulting range from the centerline algorithm is used because it would have started quite small and grown slowly until a reasonably smooth centerline was found. This idea of growing the range slowly helps to improve the contouring in situations where the gradient magnitude is small at the border of the tubular structure. Once the flood fill is complete, at S606, the contour is generated. In particular, the points that lie on the outside border of the result of the flood fill are used to generate the contour.

Figure 7A:
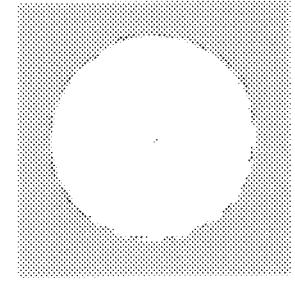
FIGS. 7A-7D illustrate various cross sectional views of a tubular structure, such as that shown in FIG. 2.
Figure 7B:
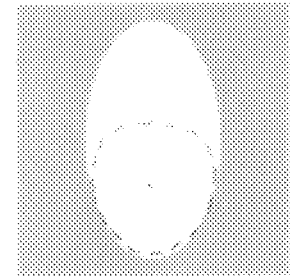
Figure 7C:
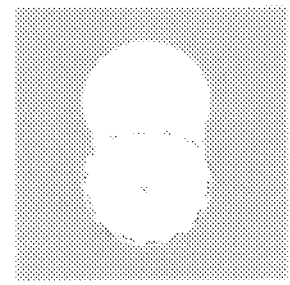
Figure 7D:
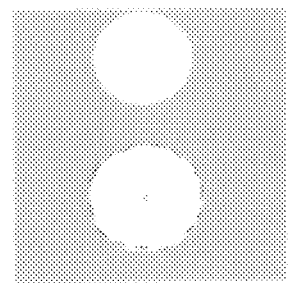

After a contour is generated, properties of the initial contour may be used to detect branch structures. For example, in accordance with aspects of the present disclosure, at S608, properties of the initial contour may be detected. Detecting branches in the tubular structure is done by measuring the following exemplary properties of the initial contour. The first property used to detect a branch is curvature. Normally with a tubular structure the curvature of the cross section contour will not change sign. Typically, a vessel has a positive curvature. If the sign of the curvature changes, that will often indicate a potential branch. This is shown in FIG. 7C, which has a cross section with negative curvature. The next property used to detect branches is the change in circularity. A tubular structure will not normally have sudden changes in circularity. When a significant change in circularity occurs that can also indicate a potential branch. FIG. 7B demonstrates this, note the location of the centerline. The other property that may be measured to detect branches is the change in area inside the contour. A sudden change in the area inside a contour can also indicate a potential branch. FIG. 7D shows a branch completing, the area inside the contour around where the centerline lies will have changed significantly. Often when these measurements indicate a branch, multiple consecutive cross section contours are identified as potential branches. Combinations of the above properties may be used to identify a bifurcation.

At S610, the contour is adjusted. Adjusting the contours so that they more closely represent the structure that the centerline is passing through can be important in many applications. Take for instance the tubular structure as a blood vessel in a computed tomography scan. Measuring stenosis in the vessel could be done using cross section contours. The contours at or near to a bifurcation could indicate a false positive.

When a branch is detected it is adjusted at S610, it by replacing the range of branch cross sections with an approximation of a non-branching tubular structure that follows the centerline. The cross section contours at each end of the branch are resampled to the same number of points. The points that make up the contours are also ordered to start at the point with the largest positive X value and follow a counterclockwise path. Spline interpolation is then used to approximate the cross section contours in between. As such, the cross sections shown in FIGS. 7A and 7C are resampled to the same resolution and reordered to start with the point at the largest positive X value and following a counterclockwise path. The dashed line in FIGS. 7B and 7C shows the adjusted result.

Figure 8:
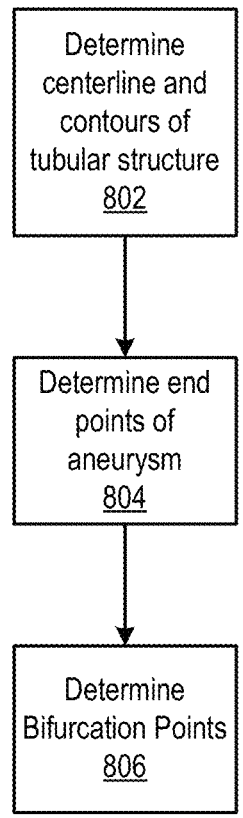
FIG. 8, there is an operational flow diagram of process performed to determine a location of an aneurysm a tubular structure, such as that shown in FIG. 2.

With reference to FIG. 8, there is an operational flow diagram of process performed to determine a location of an aneurysm. Aspects of the present disclosure may be used to determine the locations of an aneurysm. An aneurysm is a bulge in an otherwise near uniform tubular structure. The algorithm for detecting an aneurysm detects both the first and second points of the bulge plus the first bifurcation point in the tubular structure, if present, on each side of the bulge. The process begins at S802, where the previous detection of both the centerline and contours of the tubular structure is performed in accordance with the methods of FIGS. 3 and 6.

At S804, to determine the two ends of the aneurysm, the contour area may be considered as a function of position along the length of the centerline of the tubular structure. Points with a large second derivative magnitude along the centerline may be located. Such points ("marker points") are of interest because points having a large second derivative typically correspond to the neck at each end of the aneurysm, where the contour area changes abruptly from the near constant value of the tubular structure to the increasing value observed at the aneurysm ends.

At S806, the bifurcation points are determined. Knowledge of the first bifurcation points at each end of the aneurysm is typically required by a clinician. These points are located by making use of the contour area and radius in a manner similar to that described for the contour algorithm, but tuned to identify subtle bifurcations, and without the need for establishing the clean contours at each end of the bifurcation itself.

Figure 9:
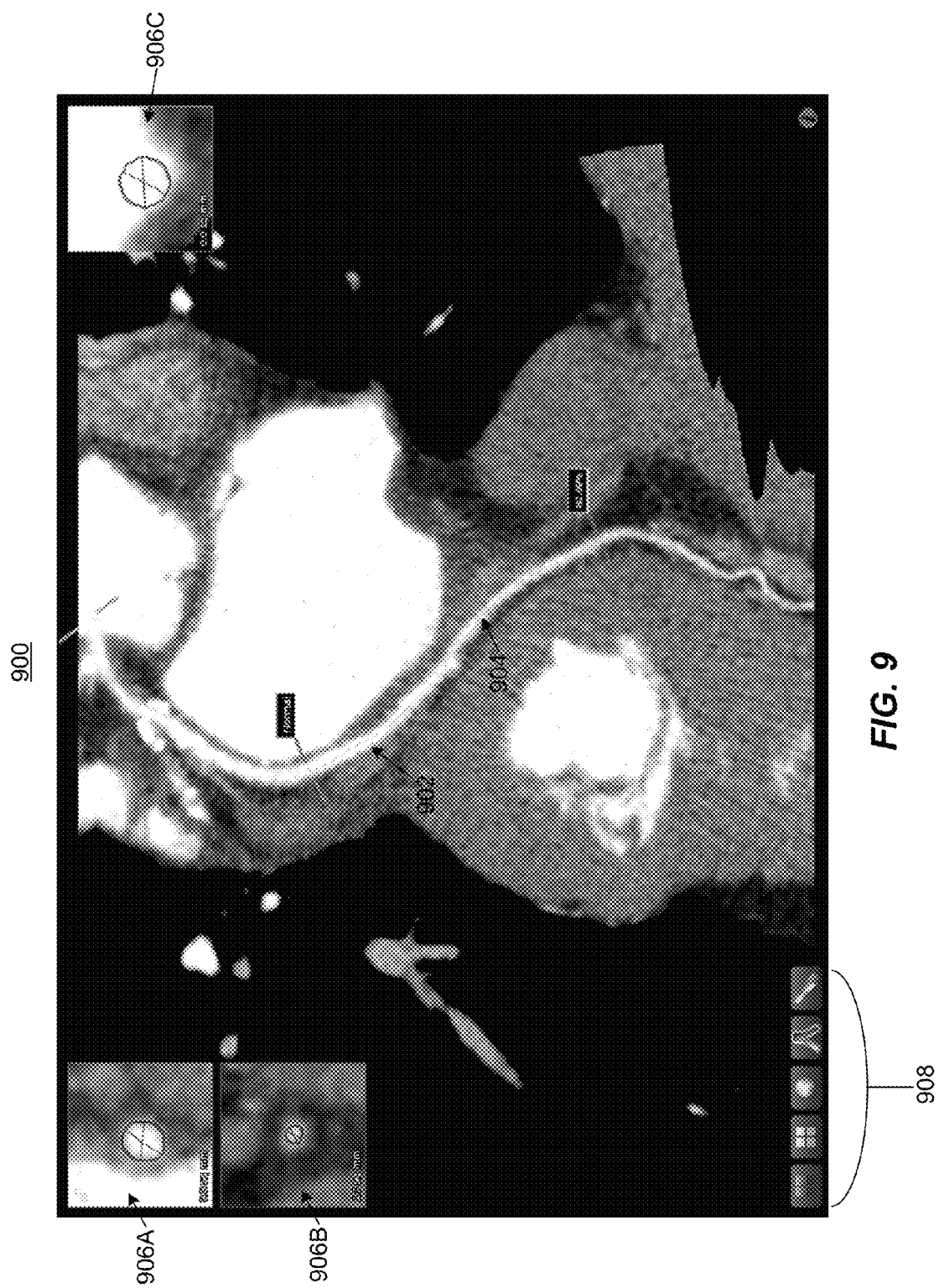
FIG. 9 illustrates an example user interface showing a visualization of the image data produced by a medical imaging system.

FIG. 9 illustrates an example user interface 900 showing a visualization of the image data produced by a medical imaging system. As shown in FIG. 9, the user interfaces displays a tubular structure 902 and a centerline 904. The user interface includes one or more windows 906A, 906B, 906C that show cross sectional views of the tubular structure 902 at selected positions. Each window 906A, 906B, 906C may display an area associated with the cross section. The user interface may further include controls 908 to allow a user to perform and apply various operations to the visualization. For example, a user may be provided functions such as pan, zoom, image flip, image rotate, point measurement, linear measurement, angle measurement, measurement calipers, etc. Other functions may be provided, such as scalpel tool, bone removal, a material editor, automated stenosis measurement, manual centerline editing, straightened vessel view, cross-sectional vessel views, vessel length measurement, vessel angle measurement, automated endograph plan with standard stenosis and measurement, marker placement, vessel lumen minimum diameter graph, vessel lumen area graph, two-click vessel centerline identification, custom description series labeling, vessel lumen minimum diameter graph, and vessel lumen area graph. The above listed functions and features are provided as a representative list. The functionalities provided by the user interface should not be construed as being limited to the above.

As noted above, the user interface may be provided on the workstation 22, which may be any connected computing device. Through an appropriate application server 20 the user interface may be rendered having characteristics appropriate for the particular device serving as the workstation 22. For example, a dedicated workstation may be provided with multiple monitors to display several views at once, whereas a mobile device may only display a limited number of views at a time (e.g., one or two). In some implementations, the application server 20 may comprise PUREWEB available from Calgary Scientific, Alberta, Canada.

A workflow associated with a user interface will now be introduced with reference to FIGS. 10-16. Generally, a user may instantiate the user interface on a workstation, such as that described above. The user interface provides options to select, edit, analyze, and generate reports regarding vessels within image data associated with, e.g., a patient. A user may initially select a particular vessel or vessels of interest to be displayed in a four quadrant view that shows, e.g., a 3D view of an area of interest and associated orthogonal 2D views of the same area of interest. Once the vessel selected, the user may edit particular properties of the vessel, such as the centerline, which may have been automatically generated in accordance with the methods above.

Once the user is satisfied with the vessel, user may enter an analysis view. Within the analysis view, user may select various functions to determine characteristics of the vessel under analysis. For example the user may determine areas of stenosis or aneurysms present in the vessel either manually or automatically by selecting an appropriate tool. The user may also edit contours associated with the vessel of interest. Other data may be displayed, such as cross-sections, diameters, areas, etc. When the user has completed the analysis of the vessel, a report may be generated to provide information in a condensed format for review by, e.g., a healthcare professional. With the introduction above, the specifics of each mode of operation, as presented in the user interface, will now be introduced.

Figure 10A:
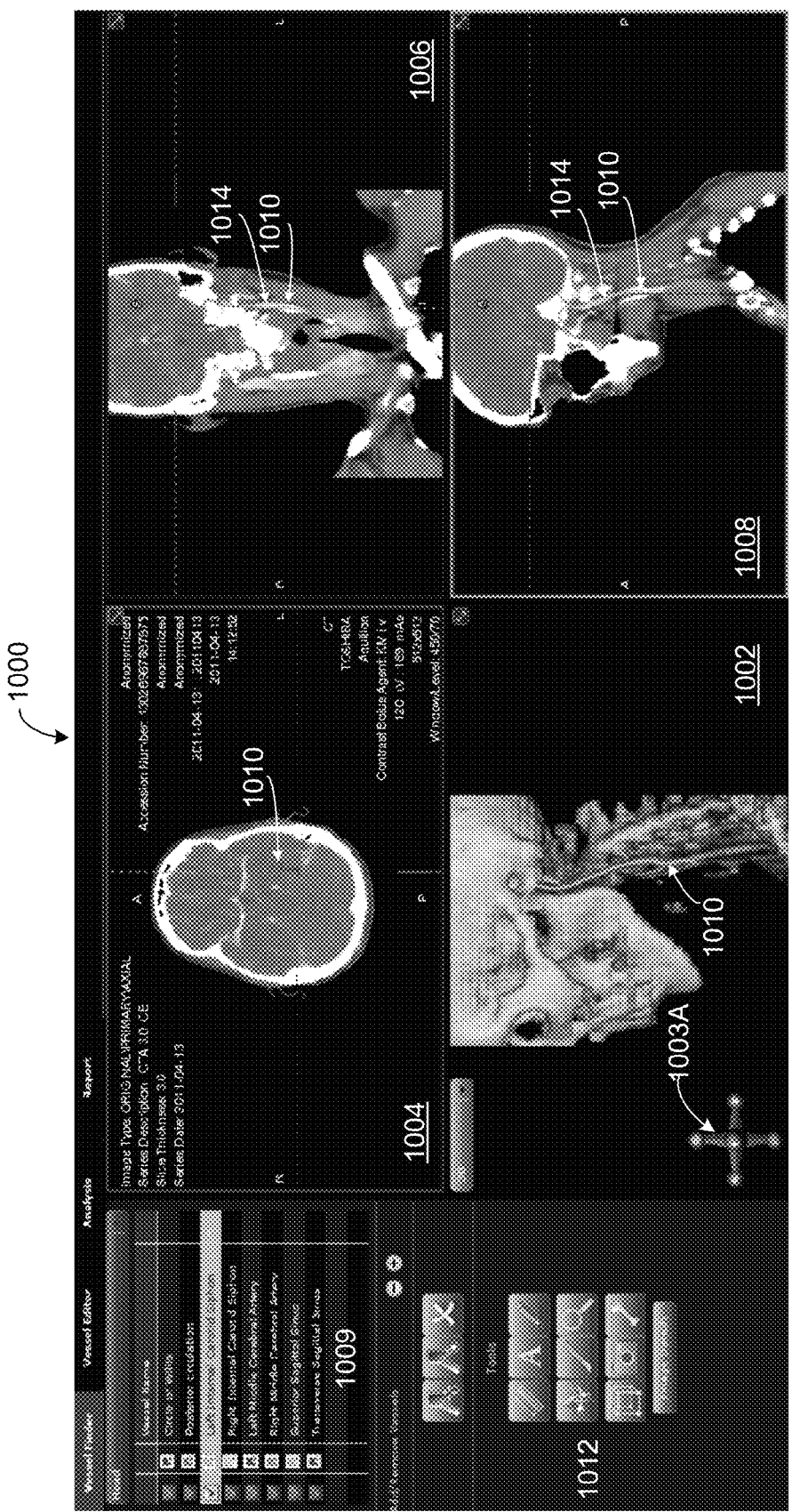
FIGS. 10A and 10B illustrate example screen shots of a user interface that may be presented on a user workstation to view image data acquired by an image processing system.
Figure 10B:
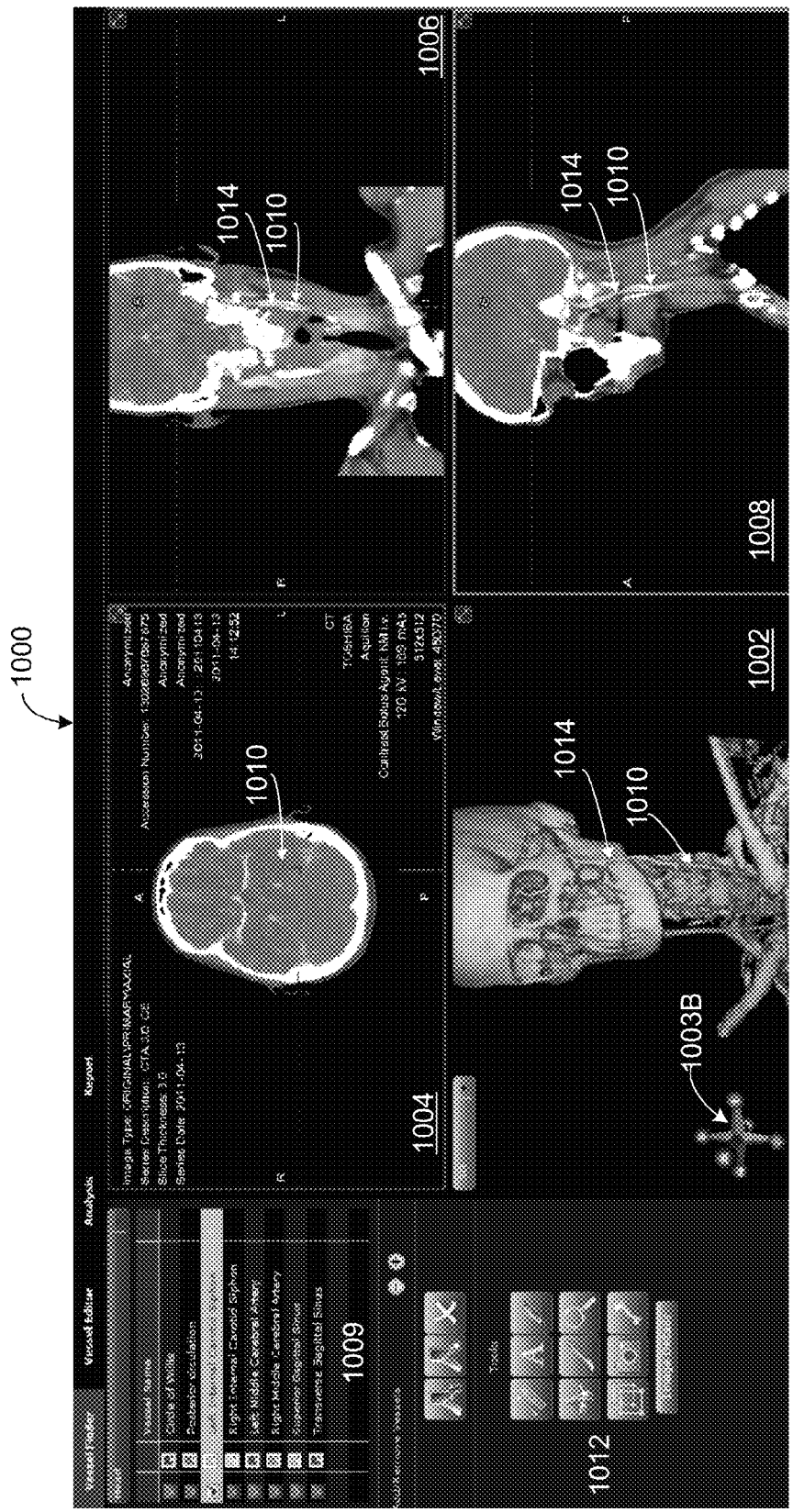

Referring now to FIGS. 10A and 10B, there are screen shots of a user interface 1000 that may be presented on, e.g., the user workstation 22 to view image data acquired by the image processing system 16. FIGS. 10A and 10B illustrate a "Vessel Finder" mode of operation. The user interface 1000 is provided on a display of the user workstation 22 to allow a user to display, annotate and/or edit a medical image generated from scans of a patient. As noted above, the user workstation 22 may be any computing device, such as a desktop computer, dedicated workstation, laptop, notebook, table computing device, mobile device (e.g., wireless hand-held smartphone), etc. As show in FIGS. 10A and 10B, the user interface 1000 enables a user to view vessels within a patient's body, display information and characteristics of the vessels (e.g., centerlines, stenosis, aneurysms, cross-sections, contours, etc.), and perform other operations such as bone removal, and cutting using a scalpel tool, etc. The user may interact with the user interface 1000 using any input devices of the user workstation 22, such as a mouse, keyboard, touchscreen, etc.

In user interface 1000, the "Vessel Finder" mode provides a 3D image 1002 of a region of a patient together with three orthogonal 2D multi-planar rendering (MPR) views 1004, 1006 and 1008. For example, the views may be an axial view, coronal view and a sagittal view, respectively. FIG. 10A shows a first orientation 1003A of the 3D image 1002 and FIG. 10B shows a second orientation 1003B of the 3D image 1002. A menu 1009 is provided to add or remove a particular vessel or vessels of interest. The available vessels are listed in the menu 1009. In some implementations, the vessels listed in the menu 1009 may be color-coded to differentiate among them when selected and shown in the various views of the user interface 1000. The available vessels may be those in which a contrast agent was injected during the imaging process performed by the medical imaging scanner 12.

In FIGS. 10A and 10B, a selected vessel 1010 (left internal carotid siphon) is shown within the brain of the patient and through the skull base (bone) and into the patient's neck. The centerline of the vessel 1010 is shown as reference numeral 1014, and may be color-coded to the vessel name shown in the menu 1009. One or more of the views 1004, 1006, 1008 may contain information about the patient, when the image data was obtained, information about the contrast agent, etc. Within the 3D window, tools 1012 are provided such that the user may perform various operations on the views, such as bone segmentation, or cutting tissue away using a scalpel function. Other tools 1012 are available, such as a lens tool, screenshot tool, a measuring tool, an annotation tool, etc., the details of which are evident to those of ordinary skill in the art.

Figure 11A:
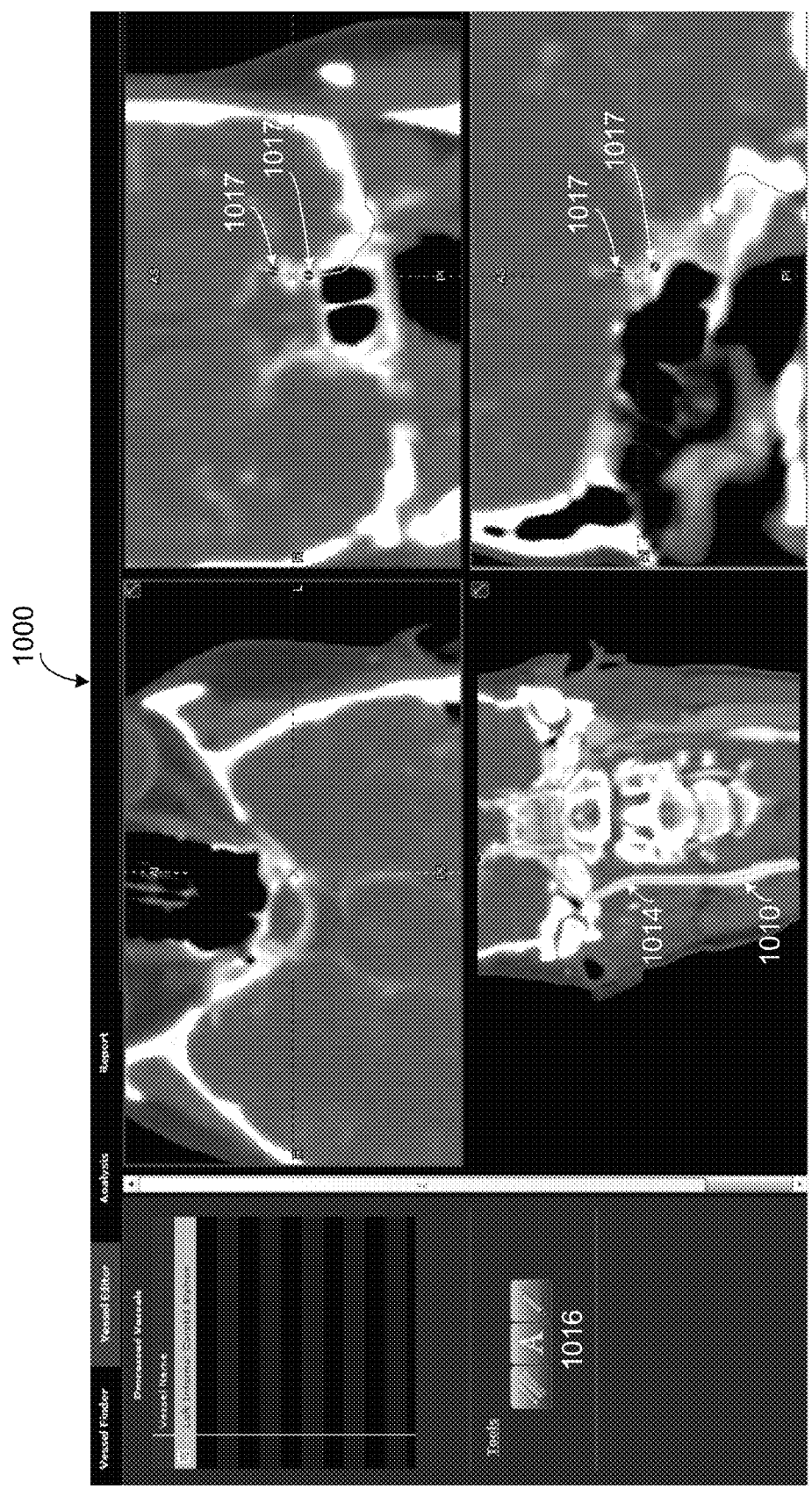
FIGS. 11A and 11B illustrate an example user interface that provides a Vessel Editor mode.
Figure 11B:
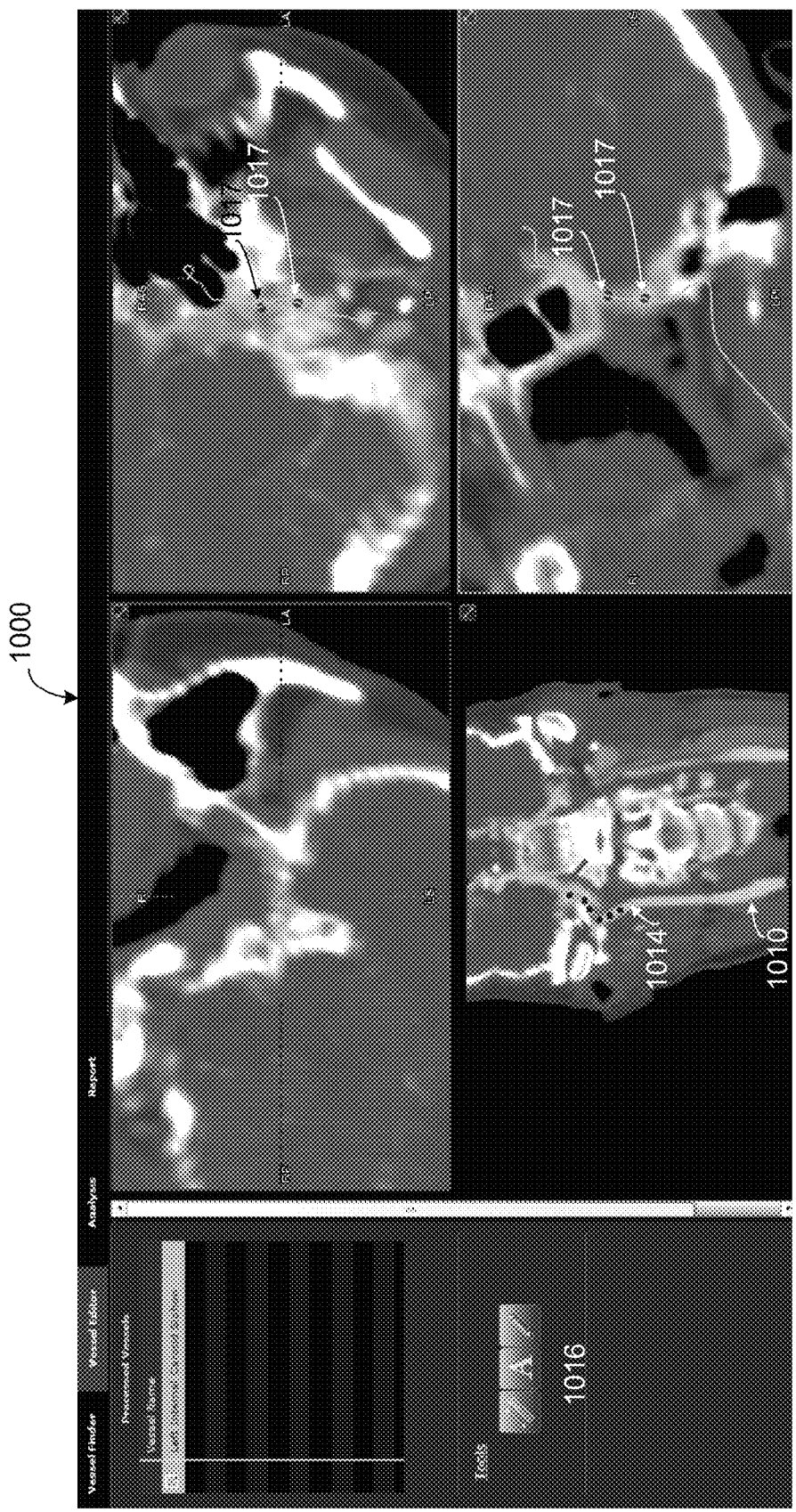

As show in FIGS. 11A and 11B, the user interface may provide a "Vessel Editor" mode, wherein a user may make adjustments to the vessel, the centerline, and other characteristics of the vessel. Adjustments may be made using one or more of the available tools 1016 showing user interface 1000. The user may, for example, may move a vessel. The user may also place a new centerline or move an existing centerline within vessel by selecting locations (shown as dots 1017) where the new location of centerline should pass. While only one vessel is shown in FIGS. 11A and 11B, it is noted that if multiple vessels are selected in the "Vessel Finder" user interface, then the multiple vessels will be shown in the "Vessel Editor" user interface. Characteristics of each vessel may be edited individually by the user.

Figure 12A:
FIGS. 12A and 12B illustrate an example user interface that provides an Analysis view.
Figure 12B:
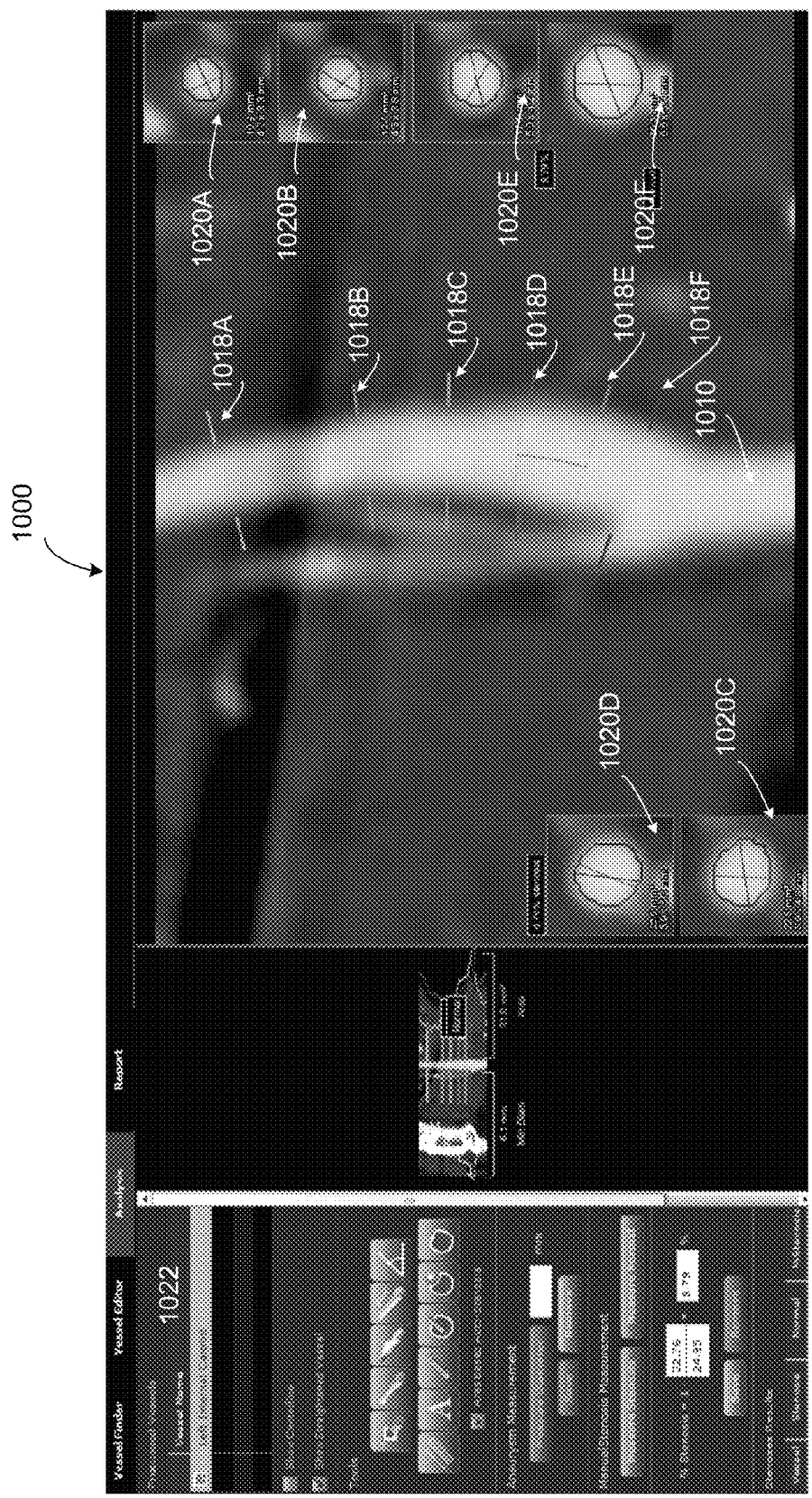
Figure 13:
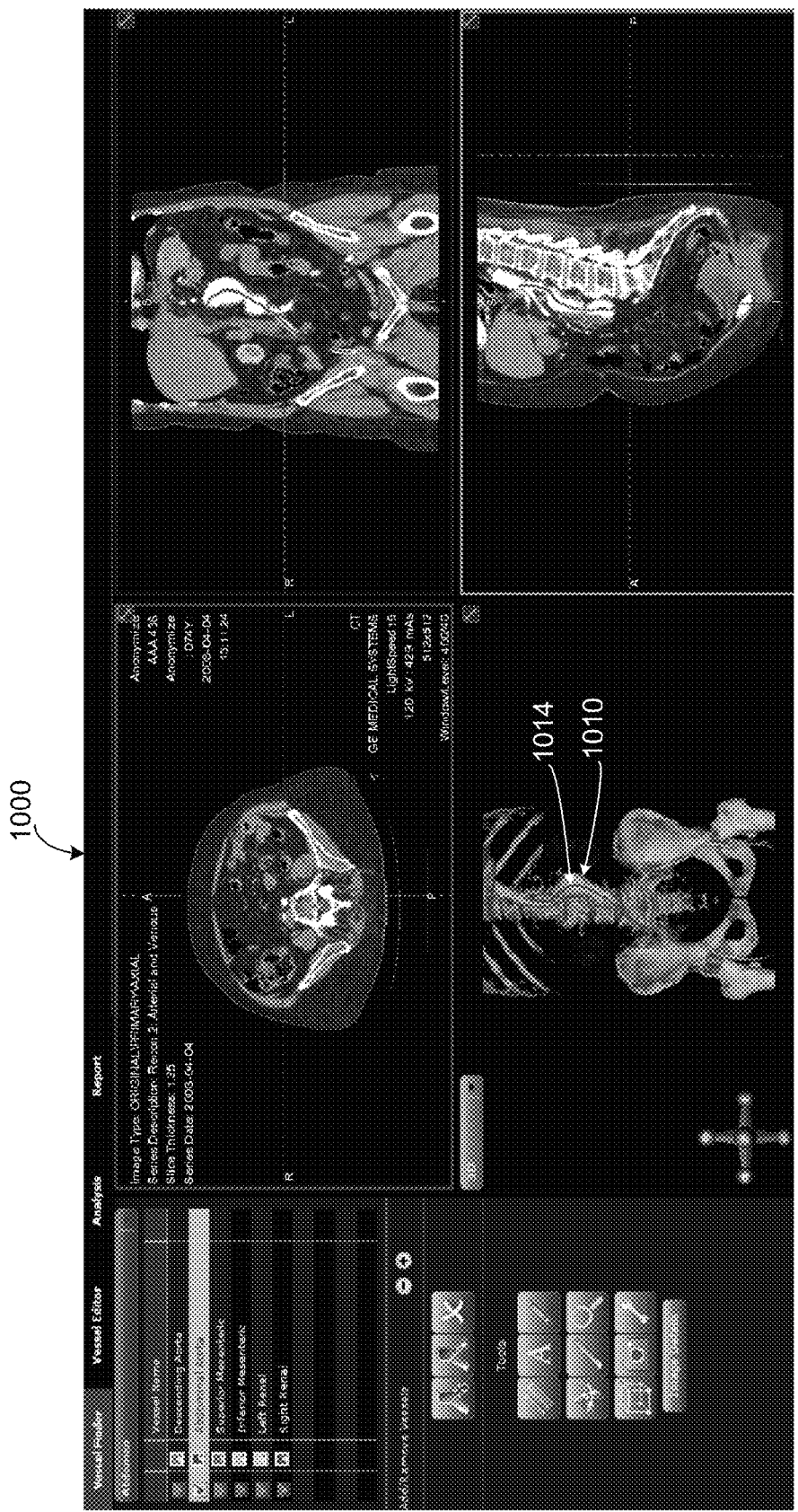
FIG. 13 illustrates and example user interface that provides a Vessel Finder mode.

FIGS. 12A and 12B illustrate an "Analysis" view of the user interface 1000. In the Analysis view, the user may select a location of the vessel to view a cross section of the vessel at that location. For example, a moveable slider 1018 may be provided perpendicular to, and centered along the edges of the vessel 1010 for the user to select a location of interest. In an associated window 1020, a cross-section of the vessel 1010 is displayed at the position where the slider 1018 is located. As the slider 1018 is moved by the user, the slider 1018 adapts to the edges of the vessel 1010, and the display of the window 1020 is updated to show the cross section at the current location of the slider 1018. As such, the window 1020 may update in real time as the slider 1018 is moved. In some implementations, the window 1020 may display the area of the cross section (e.g., 9.7 mm$^2$) and an approximate square measure (e.g., 3.7×3.4 mm). In some implementations, a contour 1024 of the vessel 1010 may be shown in the window 1020 together with maximum length and width indications 1026. As shown in FIG. 12B, the Analysis view enables multiple locations of a vessel to be simultaneously analyzed in the user interface 1000. Each location has a corresponding slider 1018A, 1018B, 1018C, 1018D, 1018E and 1018F and a respective window 1020A, 1020B, 1020C, 1020D, 1020E and 1020F, where the cross section at the slider location is shown. The sliders and the windows may be color coded to show relationships.

Within the Analysis view, multiple tools 1022 may be provided to enable a user to find or determine conditions such as, e.g., stenosis or an aneurysm of the vessel 1010. The stenosis tool may detect a broadest location of the vessel 1010 (e.g., 1018D), and from that location, user may find the most narrow location of the vessel (e.g., between 1018B and 1018D, as 1018A is not within the scope of consideration). Other tools 1022 include a puck editor that may be provide to refine the cross section of the vessel by pushing the edges to improve the contour 1024 of the vessel 1010. A contour tool may be provided to edit the contour 1024 of the vessel 1010 and to select portions of the contour 1024.

Figure 14:
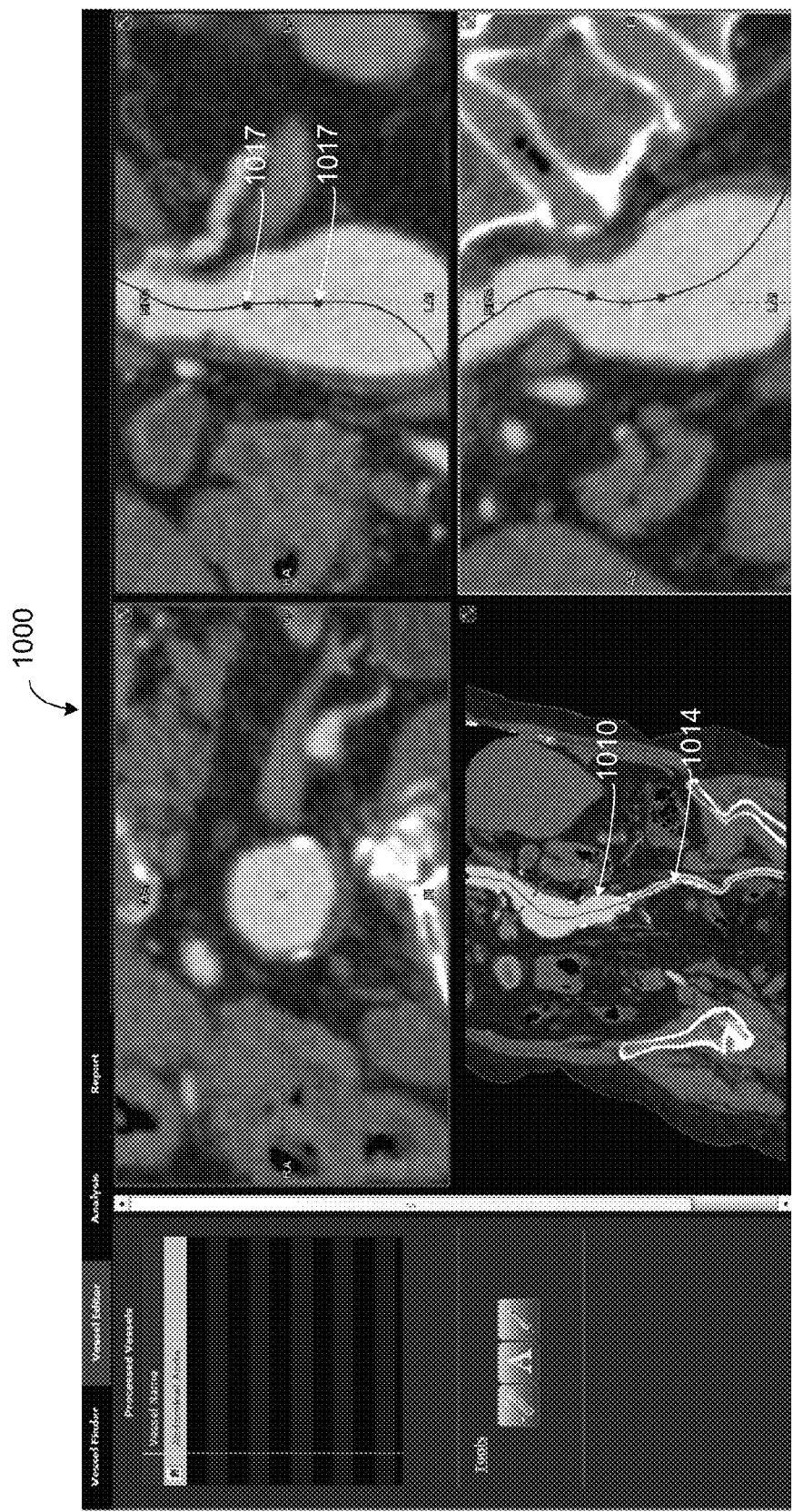
FIG. 14 illustrates another example user interface providing the Vessel Editor mode.
Figure 15:
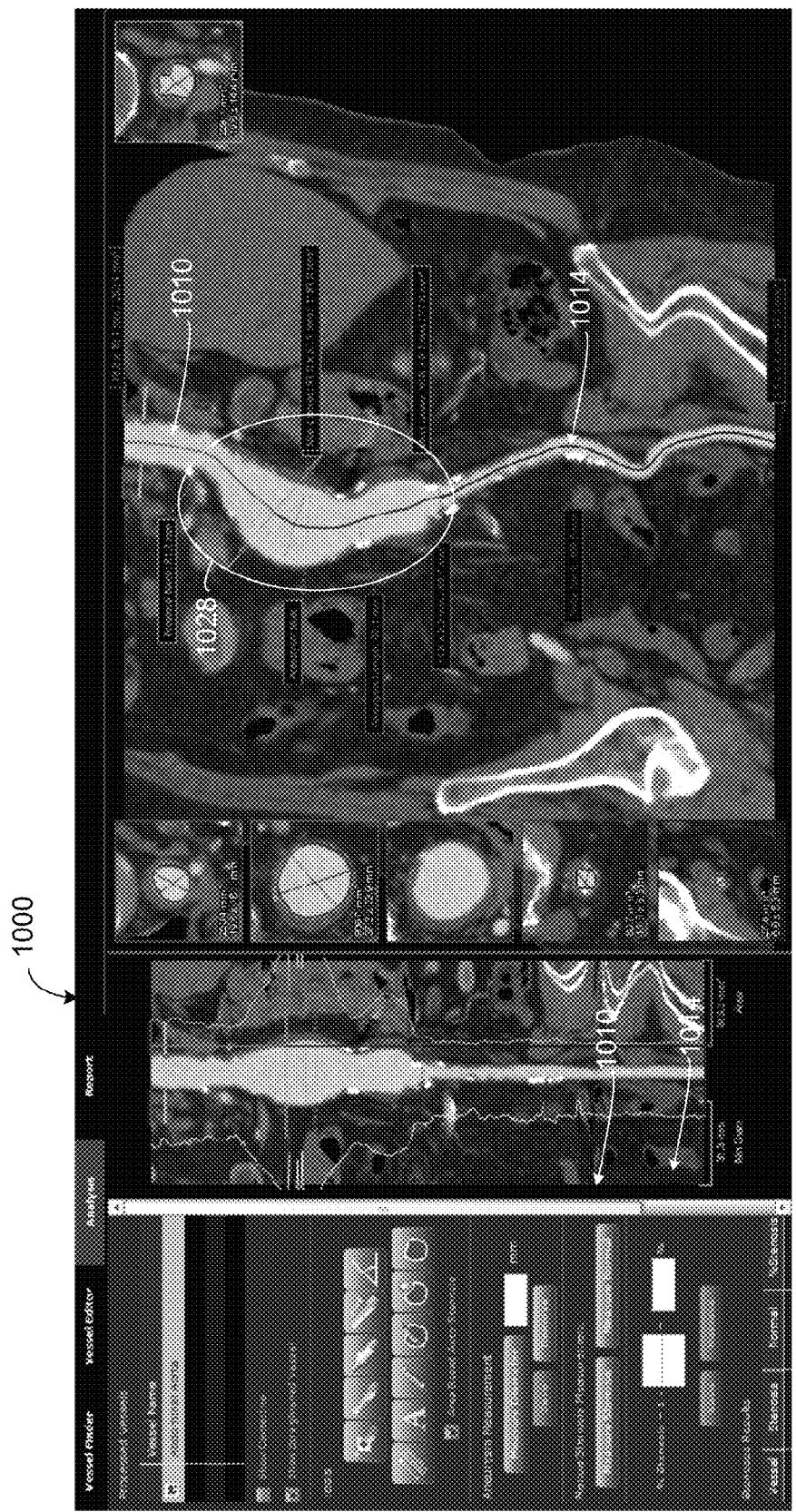
FIG. 15 illustrates another example user interface providing the Analysis mode.

In the Analysis view, an auto-aneurism tool may be provided as one of the tools 1022. In some implementations, the auto-aneurism tool may be used when analyzing, e.g., the aorta. For example, in accordance with the workflow above, the aorta is located using the Vessel Finder mode (shown as vessel 1010 in FIG. 13). As shown in FIG. 14, the accuracy of the centerline may be confirmed or refined using the Vessel Editor mode. Next, as shown in FIG. 15, in the Analysis mode, the auto aneurysm tool may locate an aneurysm 1028 and the vessel 1010, and mark several features of the vessel 1010. For example, a proximal neck and distal neck may be located. Between the necks, a maximum lumen and minimum lumen may be located, together with a cross sectional area of each. The length of the aneurism may be determined and displayed. Each of the determined features may be color-coded and a cross section of the vessel at a location of each feature shown in a respective (color-coded) window. Additionally or optionally, one or more Windows 1020 may be provided to show cross-sections of the above noted features of the vessel 1010.

Figure 16:
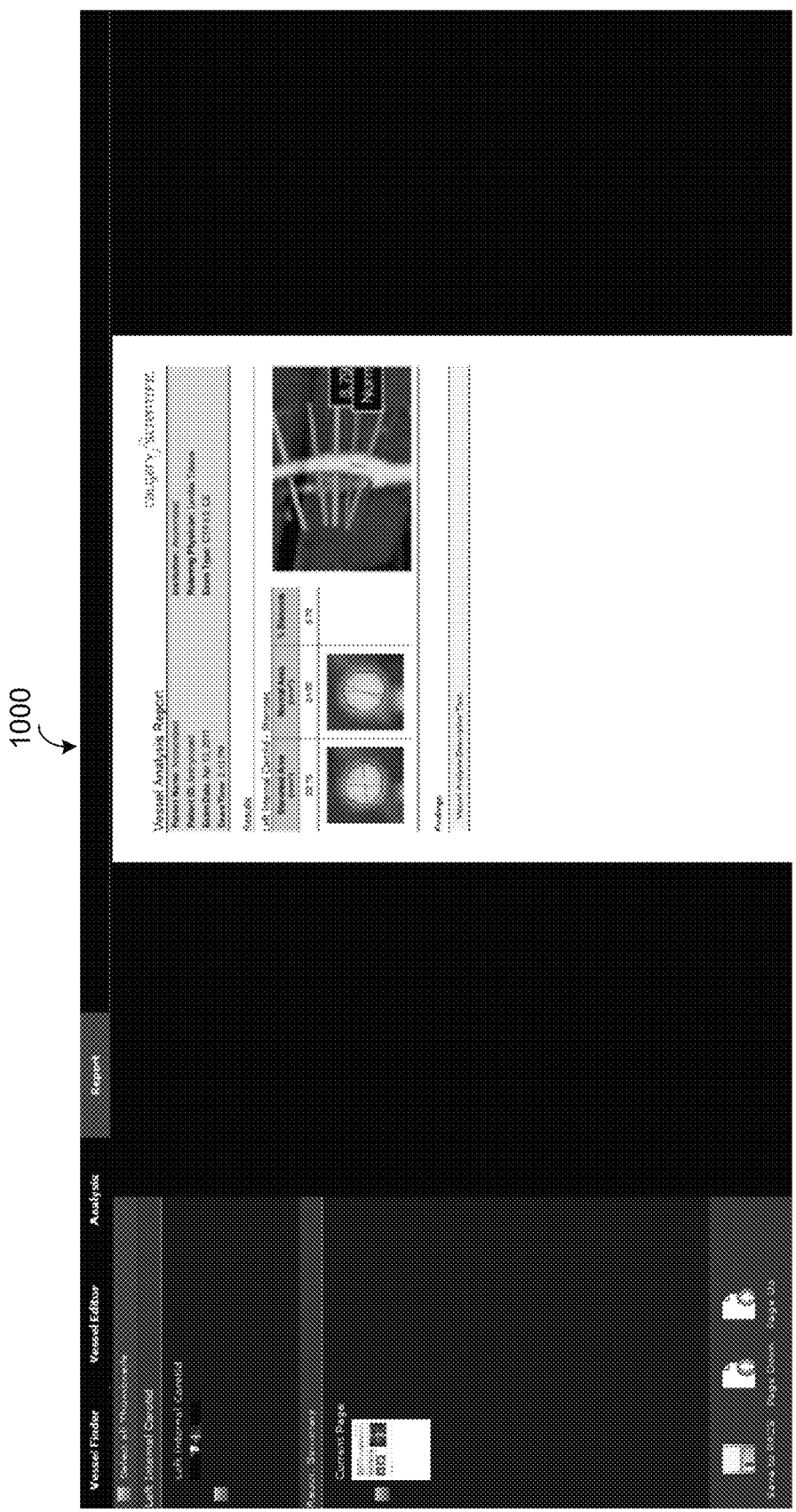
FIG. 16 illustrates an example report that may be generated from a Report user interface.

FIG. 16 illustrates an example report that may be generated from the "Report" user interface 1000. The generated report may illustrate a predetermined one or more of the views shown in the "Analysis" view user interface 1000. For example, report may show the view from FIG. 12B. The report may also show cross-sections from one or more of the windows 1020, as selected by a user. Additional or less information may be provided in the report in accordance with the particular needs of the end user.

Figure 17:
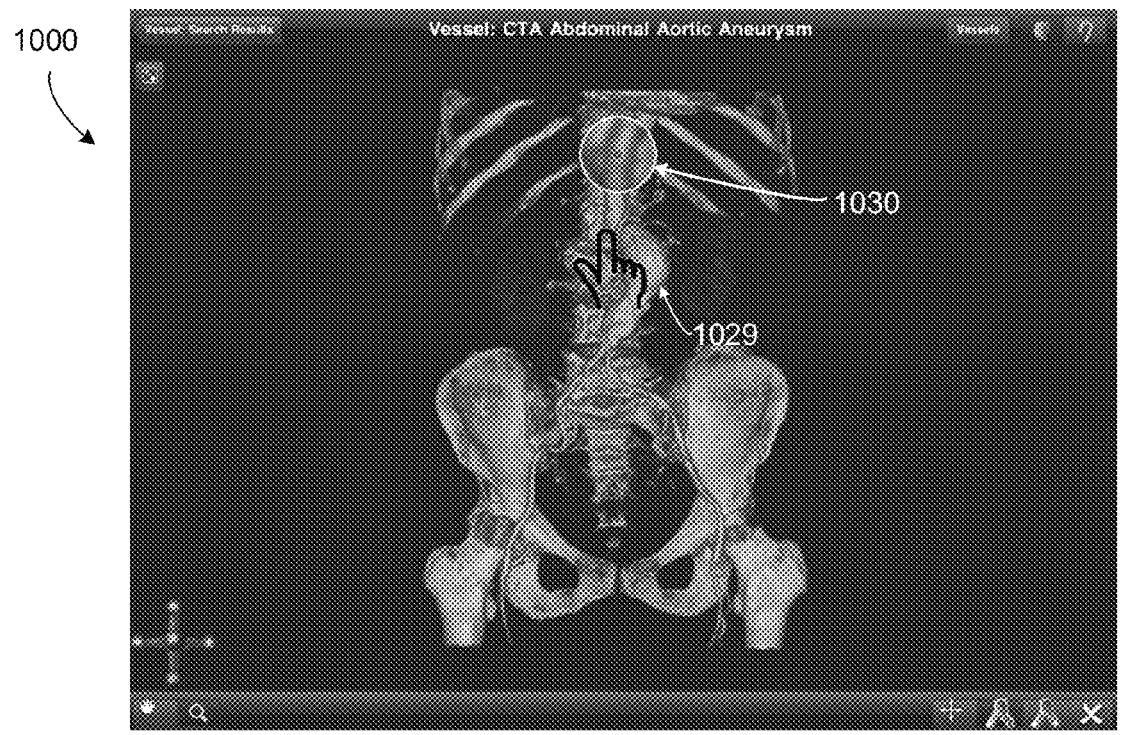
FIG. 17 illustrates an example view finder.

FIG. 17 illustrates a view finder 1030 of the user interface 1000. The view finder 1030 may be used, for example, in a touch interface to display imagery that is hidden underneath a finger 1029 that is touching the interface. The hidden imagery may be provided within the view finder 1030 as an offset window. In some implementations, the view finder 1030 may provide a zoom view of the location.

Figure 18:
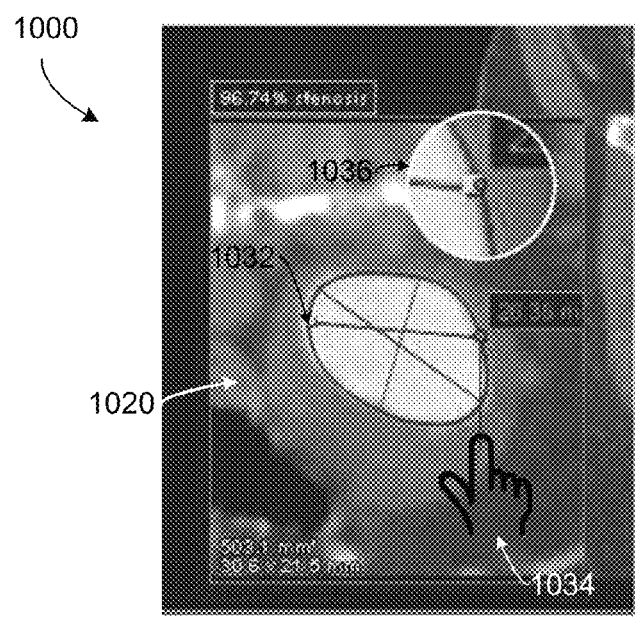
FIG. 18 illustrates an example user interface window demonstrating a touch interface interaction mode.

FIG. 18 illustrates the window 1020 demonstrating a touch interface interaction mode within the user interface 1000. In touch interfaces, mouse hover and mouse down functionalities may be reproduced using a sequential touch interaction mode. As shown, a first finger touch may be at a point 1032, which may be equivalent to moving a mouse around without depressing a button. A second finger touch at point 1034 may be an actual selection point that is offset from the first point 1030 to avoid hiding the point of interest (e.g., 1034) beneath a finger. Dot indicators may be placed at points 1032 and 1034 to enable easy visibility. In some implementations, a local zoom finder 1036 may be provided. Thus, the combination of the two finger presses allows the user to move to a precise location before starting an action such as creating a measurement.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for determining a centerline of a tubular structure using a processor of a computing device, comprising:
    receiving, at a computing device, volumetric data representative of the tubular structure and a selection of a first point and a second point along a length of the tubular structure;
    initializing a minimal range of data values associated with a cross section of the tubular structure;
    iteratively generating positions associated with two discrete curves from each point toward the other point, the positions initially moving along a direction vector defined at each point, the iteratively generating comprising:
        defining a cross section in a plane of the tubular structure;
        choosing a next point on each of the two discrete curves in accordance with a smallest area among plural cross sections determined at each next point on each of the two discrete curves;
        for each of the two discrete curves, moving in a direction normal to the cross section having the smallest area;
        determining if the discrete curves have terminated;
            if the discrete curves have terminated, then determining if a length of a result of a curve in a present iteration is shorter than a length of a curve as determined in a previous iteration; and
            caching the result of the curve in the present iteration pass if it is determined that the length of the result of the curve in the present iteration is shorter, otherwise maintaining the length of the curve as determined in the previous iteration;
    increasing the range of data values for a next iteration; and
    terminating the iterative process when a length of a joined curve is longer than a joined curve of the previous iteration, the joined curve of the previous iteration corresponding to the centerline, otherwise returning to iteratively generating positions; and
    displaying, in a user interface associated with the computing device, a visual representation of the tubular structure and the centerline in a human comprehensible format.

2. The method of claim 1, wherein initializing the data range comprises determining an area of the tubular structure at the starting point and ending point associated with range of data values.

3. The method of claim 1, wherein the two discrete curves are Non-Uniform Rational B-Spline (NURBS) curves.

4. The method of claim 1, determining the direction for each of the discrete curves comprising defining a plane at a point that describes a cross section of the tubular structure, wherein the cross section has a smallest area as compared to a second plane perturbed in a different direction several directions about the point.

5. The method of claim 1, moving in a direction normal to the cross section having the smallest area, further comprising:
    performing a local search to determine a pixel having a highest intensity; and
    moving to the pixel having the highest intensity.

6. The method of claim 1, further comprising generating a contour of the tubular structure.

7. The method of claim 6, further comprising detecting a branch in the tubular structure using at least one of detecting curvature of the tubular structure, detecting a change in circularity of the tubular structure, and measuring a change in area inside the contour.

8. The method of claim 6, further comprising adjusting the contour by replacing the range of data values the cross sections associated with the branch with an approximation of the range of data values in a non-branching tubular structure.

9. The method of claim 8, further comprising:
determining an aneurysm in the tubular structure by determining ends of the aneurysm by considering an area of the contour area as a function of position along a length of the centerline of the tubular structure; and
locating marker points along the length with a large second derivative magnitude,
wherein the marker points correspond to a neck at each end of the aneurysm.

10. The method of claim 1, wherein the volumetric data is a multi-dimensional medical image.

11. The method of claim 1, wherein the tubular structure is a vessel.

12. The method of claim 11, wherein the vessel is located near bone or the base of the skull.

13. A method for determining a shortest path between two points of a tubular structure using a processor of a computing device, comprising:
receiving, at a computing device, volumetric data representative of the tubular structure and a selection of a first point and a second point along a length of the tubular structure;
initializing a minimal range of data values associated with a cross section of the tubular structure; and
iteratively generating positions associated with two discrete curves from each point toward the other point, the positions initially moving along a direction vector defined at each point toward each other point until it is determined if the two discrete curves have terminated or if the two discrete curves have joined,
if the two discrete curves have terminated, further determining if an incomplete result is better than a previous incomplete result and updating a cache if the incomplete result is better; and
if the two discrete curves have joined, further determining if a complete result is better than a previous complete result and updating the cache if the complete result is better; and
displaying, in a user interface associated with the computing device, a visual representation of the tubular structure and the shortest path in a human comprehensible format.

14. The method of claim 13, further comprising:
at a current point on each of the two discrete curves, defining a plane in the tubular structure perpendicular to a current direction vector and passing through the current point, the plane defining a cross section of the tubular structure;
choosing a next point on each of the two discrete curves, the next point being associated with the cross section having a smallest area among plural cross sections determined at the next point on each of the two discrete curves; and
for each of the two discrete curves, moving in a direction normal to the cross section having the smallest area.

15. The method of claim 13, choosing a next point on each of the two discrete curves, further comprising:
performing a local search to determine a pixel having a highest intensity; and
moving to the pixel having the highest intensity.

16. The method of claim 13, further comprising increasing the range of data values for a next iteration.

17. The method of claim 16, further comprising:
determining if the range has grown to greater than a predetermined number of times larger than an initial range;
determining if the centerline has been determined; and
if so, providing the centerline as a results; and
if not, providing the incomplete result from the cache.

18. The method of claim 13, wherein if the two discrete curves have not terminated and the two discrete curves have not joined, the method further comprising:
determining if the incomplete result is better than a previous incomplete result during a same iteration and updating a cache if the incomplete result is better that the previous incomplete result during the same iteration.

19. The method of claim 13, wherein if the two discrete curves have terminated, the determining is performed in accordance with the following relationship:
if (gap>=distance)

quality=0 otherwise quality=(distance−gap)×(distance−gap)/(distance×length), wherein the distance equals a distance between two starting points, the length equals a total length of the two discrete curves, a gap equals a remaining distance between final end points of the two discrete curves, and the quality ranges from 0 to 1, with 1 being a best theoretical achievable quality.

20. The method of claim 13, wherein the tubular structure is a vessel.

* * * * *